United States Patent [19]

Crane et al.

[11] Patent No.: US 6,284,717 B1
[45] Date of Patent: Sep. 4, 2001

(54) DISPERSANT ADDITIVES

(75) Inventors: Anthony E. Crane, Cheshire; Richard M. Scott, Kent, both of (GB)

(73) Assignee: Infineum USA L.P., Linden, NJ (US)

(*) Notice: Subject to any disclaimer, the term of this patent is extended or adjusted under 35 U.S.C. 154(b) by 0 days.

(21) Appl. No.: 09/432,739

(22) Filed: Nov. 2, 1999

(30) Foreign Application Priority Data

Dec. 22, 1998 (EP) .................................................. 98310565

(51) Int. Cl.[7] .................. C10M 133/42; C10M 133/16; C10M 133/46; C07D 251/70; C07D 403/02
(52) U.S. Cl. ........................... 508/258; 544/196; 544/198
(58) Field of Search ............................ 508/258; 544/196, 544/198

(56) References Cited

U.S. PATENT DOCUMENTS

| 3,785,981 | * | 1/1974 | Hotten . |
| 3,928,344 | * | 12/1975 | Westlinning et al. . |
| 4,642,344 | * | 2/1987 | Hajek et al. . |
| 4,824,845 | * | 4/1989 | Gehret et al. . |
| 5,536,766 | * | 7/1996 | Seyffer et al. . |
| 5,807,929 | * | 9/1998 | Lin et al. . |
| 6,013,797 | * | 1/2000 | Lin et al. . |
| 6,096,244 | * | 8/2000 | Graichen . |

FOREIGN PATENT DOCUMENTS

| 0 240 867 B1 | 2/1992 | (EP) | ............................ C07D/251/70 |
| 0 285 609 B1 | 2/1994 | (EP) | ............................ C08F/287/00 |
| 0 287 569 B1 | 2/1994 | (EP) | ............................ C10M/143/12 |
| 949981 | 2/1964 | (GB) . | |
| 1483729 | 8/1977 | (GB) | ............................ C08F/8/46 |

* cited by examiner

Primary Examiner—Jerry D. Johnson

(57) ABSTRACT

The reaction product of:
(i) a polyalkenyl derivative of an ethylenically unsaturated carboxylic reagent and
(ii) a compound of the formula

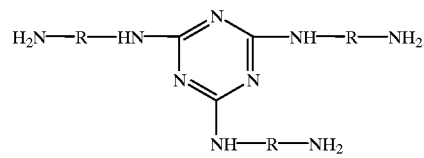

wherein R is a linear alkylene group having at least 2 carbon atoms, a branched alkylene group having at least 3 carbon atoms, a cycloalkylene group having at least 5 carbon atoms, in which one or more of said carbon atoms may be substituted by one or more hetero atoms, or is an aromatic group or a group of the formula in which a is 1 to 6 and b is 0 to 6, wherein the groups R may be the same or different, and wherein the values of a and b may be the same or different; process for the preparation of said reaction product; lubricating oil compositions, fuel compositions and additive concentrates containing such reaction products; and use of the reaction products as dispersant additives.

10 Claims, 3 Drawing Sheets

DISPERSANT ADDITIVES

Figure 1:
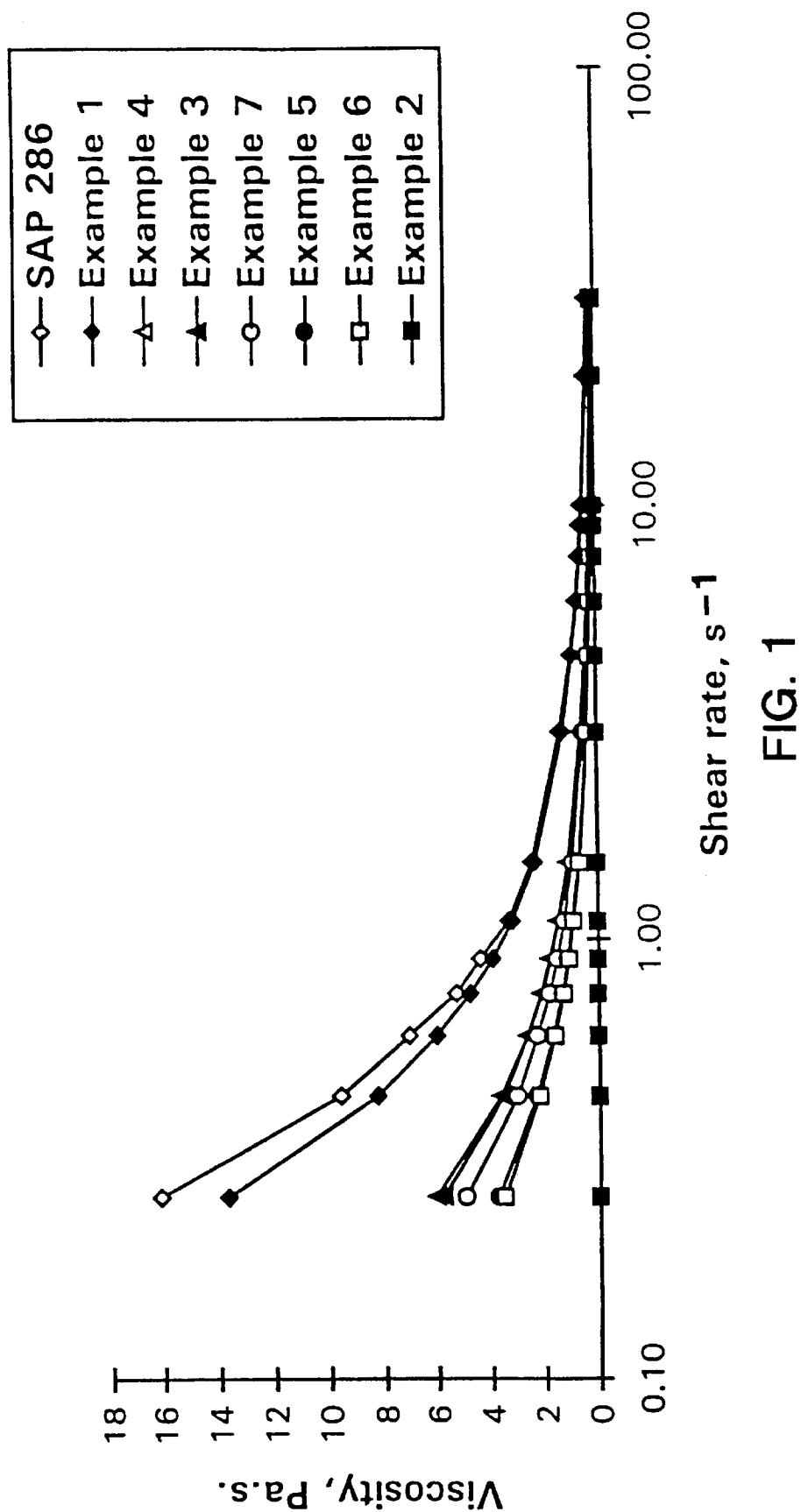

The present invention relates to triazine derivatives, a process for their preparation, lubricating oil compositions, fuel compositions and additive concentrates containing them and their use as dispersant additives.

In accordance with the present invention there is provided the reaction product of:
(i) a polyalkenyl derivative of an ethylenically unsaturated carboxylic reagent and
(ii) a compound of the formula

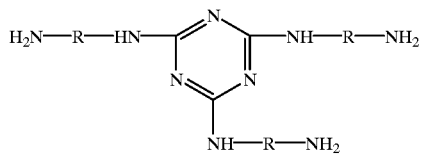

wherein R is a linear alkylene group having at least 2 carbon atoms, a branched alkylene group having at least 3 carbon atoms, a cycloalkylene group having at least 5 carbon atoms, in which one or more of said carbon atoms may be substituted by one or more hetero atoms, or is an aromatic group or a group of the formula

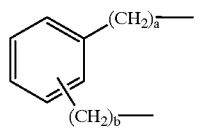

in which a is 1 to 6 and b is 0 to 6, wherein the groups R may be the same or different, and wherein the values of a and b may be the same or different.

The ethylenically unsaturated carboxylic reagent contains a total of at least 3 carbon atoms, preferably a total of from 3 to 50, more preferably from 3 to 30, still more preferably from 4 to 20, and even more preferably from 4 to 10, carbon atoms.

The ethylenically unsaturated carboxylic reagent may be an alpha-beta olefinic unsaturated carboxylic reagent as described at page 6, lines 15 to 48 of EP-B-0285609 or page 6, lines 11 to 39 of EP-B-0287569, e.g. acrylic acid ($C_3$), methacrylic acid ($C_4$), cinnamic acid ($C_9$), crotonic acid ($C_4$), 2-phenylpropenoic acid ($C_9$), maleic acid ($C_4$), fumaric acid ($C_4$), glutaconic acid ($C_5$), mesaconic acid ($C_5$), itaconic acid (methylene succinic acid) ($C_5$), citraconic acid (methyl maleic acid) ($C_5$) and functional derivatives thereof such as anhydrides (e.g. maleic anhydride ($C_4$), glutaconic anhydride ($C_5$), itaconic anhydride ($C_5$), citraconic anhydride ($C_5$)), esters (e.g. methyl acrylate ($C_4$)), amides, imides, salts, acyl halides and nitriles.

Preferably the ethylenically unsaturated carboxylic reagent is selected from monoethylenically unsaturated $C_4$–$C_{10}$ dicarboxylic acids and anhydrides, of which maleic anhydride is most preferred.

The polyalkenyl derivative of an ethylenically unsaturated carboxylic reagent may be prepared by methods known in the art. For example, if the ethylenically unsaturated carboxylic reagent is maleic anhydride, the polyalkenyl derivative thereof may conveniently be prepared by mixing a polyalkene with a specified amount of maleic anhydride and passing chlorine through the mixture, e.g. as described in GB-A-949981. Alternatively, the derivative may be prepared by reacting thermally, at an appropriate temperature, the polyalkene with a specified amount of maleic anhydride, e.g. as described in GB-A-1483729. In EP-A-0542380 is described a process for preparing such a derivative, which involves reacting the polyalkene with maleic anhydride in a mol ratio of maleic anhydride to polyalkene of greater than 1:1, at a temperature in the range from 150 to 260° C. and in the presence of a polyaddition-inhibiting amount of a sulphonic acid. The molar ratio of ethylenically unsaturated carboxylic moiety to polyalkenyl moiety in the derivative formed is preferably 1:1 to 5:1, more preferably 1:1 to 3.5:1, particularly 1.5:1 to 2:1.

The polyalkene used to prepare the polyalkene derivative may be a homopolymer or copolymer, for example of at least one $C_{2-10}$ monoolefin. Preferably the polyalkene is a polymer of at least one $C_{2-5}$ monoolefin, e.g. an ethylene-propylene copolymer. The monoolefin is preferably a $C_{3-4}$ olefin, in particular propylene or isobutylene, and preferred polyalkenes derived therefrom include polyisobutylenes and atactic or isotactic or syndiotactic propylene oligomers. Polyisobutylenes such as that sold by BASF under the trade mark "GLISSOPAL" and those sold by the British Petroleum Company under the trade marks "ULTRAVIS" (both having high levels (about 80 to 90%) of terminal vinylidene unsaturation), "HYVIS" and "NAPVIS", e.g. "HYVIS 75", "HYVIS 120", "HYVIS 200", "NAPVIS 10" and "NAPVIS 120" polyisobutylenes, are especially preferred for use in the present invention.

The polyalkene has a number average molecular weight ($M_n$) preferably in the range from 300 to 7000, more preferably from 500 to 5000, still more preferably from 700 to 3000.

Compounds of the formula of reactant (ii) and their preparation are described in EP-B-0240867. In said compounds, when R is a linear alkylene group it preferably contains 2 to 20 carbon atoms, more preferably 2 to 16 carbon atoms, particularly 2 to 12 carbon atoms, especially ethylene, propylene, butylene, pentylene and hexylene groups. When R is a branched alkylene group, it preferably contains 3 to 20 carbon atoms, more preferably 3 to 15 carbon atoms, particularly where the branches comprise low alkyl groups such as methyl, ethyl and propyl. When R is a cycloalkylene group, it is preferably a 1,2-cyclohexyl, 1,3-cyclohexyl or 1,4-cyclohexyl group. One or more, preferably 2 or 3, of the carbon atoms in said groups R may be substituted by heteroatoms selected from oxygen and sulphur atoms, or nitrogen atoms in the form of the group —NHR'—, wherein R' can be various moieties, in particular an alkyl group, more preferably containing 1 to 6 carbon atoms, or a hydrogen atom. When R is an aromatic group, it is preferably a phenylene or naphthylene group, particularly an ortho-, meta- on para-phenylene group. Such an aromatic group may be substituted, for example by one or more halogen atoms, alkyl groups, alkoxy groups, hydroxyl groups and equivalent groups. When R is a group of the formula

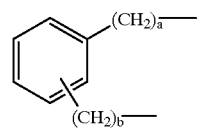

it is optionally substituted in the core or the side-chains by substituents referred to above in relation to the aromatic groups. Compounds of particular interest include tris-(6-aminohexyl)-melamine (i.e. each group of R is hexylene) ("TAHM").

The present invention further provides a process for the preparation of a reaction product as defined above which comprises reacting
(i) a polyalkenyl derivative of an ethylenically unsaturated carboxylic reagent and
(ii) a compound of the formula

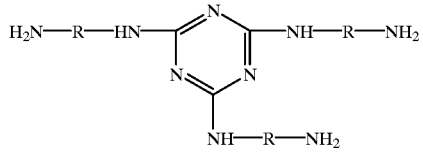

wherein R is a linear alkylene group having at least 2 carbon atoms, a branched alkylene group having at least 3 carbon atoms, a cycloalkylene group having at least 5 carbon atoms, in which one or more of said carbon atoms may be substituted by one or more hetero atoms, or is an aromatic group or a group of the formula

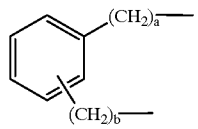

in which a is 1 to 6 and b is 0 to 6, wherein the groups R may be the same or different, and wherein the values of a and b may be the same or different.

The reaction between (i) and (ii) is conveniently carried out in the presence of a suitable solvent at elevated temperature (i.e. above ambient temperature (20° C.)), e.g. in the temperature range 120 to 240° C., more particularly 140 to 200° C., often under reflux conditions and, where necessary, at elevated pressure, e.g. in the range from 2 to $100 \times 10^5$ Pa. Examples of solvents include hydrocarbon solvents such as higher alkanes, toluene, xylene, mesitylene, e.g "SHELLSOL" (trade mark) A solvent available from member companies of the Royal Dutch/Shell Group of Companies; also synthetic and mineral oils such as "HVI-60"; ether solvents such as tetrahydrofuran and 1,4-dioxane; nitriles such as acetonitrile; alcohols such as 1-pentanol (amyl alcohol) and 2-methyl-2-propanol (tert-butyl alcohol); and chlorohydrocarbons such as 1,1,1-trichloroethane. The process may be carried out in the absence of a solvent but, as indicated above, is conveniently carried out in the presence of one. Any water or excess of alcohol may be removed using for example a Dean and Stark trap.

The molar ratio (i):(ii) in the process of the present invention is preferably in the range from 1:1 to 4:1, more preferably from 1:1 to 3:1, most preferably from 1:1 to 2:1.

The reaction product of the present invention may be used as an additive in lubricating oils. Accordingly, the present invention provides a lubricating oil composition comprising a major amount (more than 50% w) of a lubricating base oil and a minor amount (less than 50% w), preferably from 0.1 to 20% w, especially from 0.5 to 10% w (active matter), of a reaction product according to the present invention, the percentages by weight being based on the total weight of the composition.

A lubricant formulation may be produced by addition of an additive package to the lubricating oil. A minor amount of viscosity modifier may be included if the final lubricant formulation is to be a multigrade version. The type and amount of additive package used in the formulation depends on the final application, which can include spark-ignition and compression-ignition internal combustion engines, including automobile and truck engines, marine and railroad diesel engines, gas engines, stationary power engines and turbines.

The lubricant formulation is blended to meet a series of performance specifications as classified in the US by a tripartite arrangement between the Society of Automotive Engineers (SAE), American Petroleum Institute (API) and American Society for Testing and Materials (ASTM). Also the American Automobile Manufacturers Association (AAMA) and Japan Automobile Manufacturers Association Inc. (JAMA), via an organisation called the International Lubricant Standardisation and Approval Committee (ILSAC), jointly develop minimum performance standards for gasoline-fuelled passenger car engine oils.

In Europe, engine oil classifications are set by the Association des Constructeurs Europeens de l'Automobile (ACEA) in consultation with the Technical Committee of Petroleum Additive Manufacturers (ATC) and Association Technique de l'Industries Europeens des Lubrifiants (ATIEL). Besides these internationally recognised oil classification systems, many, if not all, Original Equipment Manufacturers (OEMs) have their own in-house performance requirements that must be met by lubricant formulations used for first (i.e. factory) fill.

Suitable lubricating base oils are natural, mineral or synthetic lubricating oils.

Natural lubricating oils include animal and vegetable oils, such as castor oil. Mineral oils comprise the lubricating oil fractions derived from crude oils, e.g. of the naphthenic or paraffinic types or mixtures thereof, coal or shale, which fractions may have been subjected to certain treatments such as clay-acid, solvent or hydrogenation treatments. Synthetic lubricating oils include synthetic polymers of hydrocarbons, e.g. derived from polyalphaolefins, isomerised slack wax, modified alkylene oxide polymers and esters, which are known in the art. These lubricating oils are preferably crankcase lubricating oil formulations for spark-ignition and compression-ignition engines, but include also hydraulic lubricants, metal-working fluids and automatic transmission fluids.

Preferably the lubricating base oil component of the compositions according to the present invention is a mineral lubricating oil or a mixture of mineral lubricating oils, such as those sold by member companies of the Royal Dutch/Shell Group of Companies under the designations "HVI", or the synthetic hydrocarbon base oils sold by member companies of the Royal Dutch/Shell Group of Companies under the designation "XHVI" (trade mark).

The viscosity of the lubricating base oils present in the compositions according to the present invention may vary within wide ranges, and is generally from 3 to 35 $mm^2/s$ at 100° C.

The lubricating oil compositions according to the present invention may contain various other additives known in the art, such as:

(a) Viscosity index improvers or modifiers. The viscosity modifier may be of the solid type or a concentrate in a natural or synthetic base stock and can be defined as a substance, usually a polymer, which substantially improves (e.g. by at least 5 units) the viscosity index (e.g. as determined by ASTM procedure D2270) by its incorporation. These can all be incorporated into the final lubricant formulation to give the desired performance properties thereof. Examples of such viscosity modifiers are linear or star-shaped polymers of a diene such as isoprene or butadiene, or a copolymer of such a diene with optionally substituted styrene. These copolymers are suitably block copolymers and are preferably hydrogenated to such an extent as to saturate most of the olefinic unsaturation. A number of other types of viscosity modifier are known in the art, and many of these are described in Proceedings of Conference "Viscosity and flow properties of multigrade engine oils", Esslingen, Germany, December 1977. It is also known in the art that viscosity modifiers can be functionalised to incorporate dispersancy (e.g. dispersant viscosity index improvers based on block copolymers, or polymethacrylates) and/or antioxidant functionality as well as viscosity modification and they can also have pour point depressants mixed in to give handleable products in cold climates.

(b) Ashless or ash-containing extreme pressure/anti-wear additives, such as, for example, those of the metal containing dithiophosphate or ashless dithiocarbamate type, and mixtures thereof. The actual composition of the individual components will vary depending upon final application and hence can be based on a range of metal ion types and various alcohols, in which both alkyl and aryl moieties may be of varying size. Preferred are zinc dithiophosphates (ZDTPs) or sodium dithiophosphates.

(c) Dispersants including succinimides and Mannich bases, both of various molecular weights and amine type, including borated versions, or esters also of varying type and molecular weight. Preferred are ashless dispersants such as polyolefin-substituted succinimides, e.g. those described in GB-A-2231873.

(d) Anti-oxidants, for example of the aminic type such as "IRGANOX" (trade mark) L57 (tertiary $C_4$–$C_{12}$ alkyl diphenylamine) or phenolic type such as "IRGANOX" (trade mark) L135 (2,6-ditertiary-butyl-4-(2-carboxy(alkyl)ethyl)phenol) (ex. CIBA Speciality Chemicals) or a soluble copper compound at a copper concentration of between 50 and 500 ppm.

(e) Anti-rust compounds of, for example, the ethylene/propylene block copolymer type.

(f) Friction modifiers for fuel economy, either metal (e.g. molybdenum) containing, or metal free esters and amines, or synergistic mixtures thereof.

(g) Metal containing detergents such as phenates, sulphonates, salicylates or naphthenates, or mixtures thereof, all of which detergents may be either neutral or overbased, such overbased detergents being carbonates, hydroxides or mixtures thereof. The metals are preferably calcium, magnesium or manganese, although alkali metals such as sodium or potassium could also be used.

(h) Copper passivators, preferably of the alkylated or benzylated triazole type.

The reaction product of the present invention may also be used as an additive in fuels. Accordingly, the present invention further provides a fuel composition comprising a major amount (more than 50% w) of a base fuel and a minor amount (less than 50% w), preferably from 0.001 to 2% w, more preferably from 0.001 to 0.5% w and especially from 0.002 to 0.2% w (active matter), of a reaction product according to the present invention, the percentages by weight being based on the total weight of the composition.

Suitable base fuels include gasoline and diesel fuel. These base fuels may comprise mixtures of saturated, olefinic and aromatic hydrocarbons, and may contain a range of sulphur levels, e.g. in the range 0.001 to 0.1% w. They can be derived from straight-run gasoline, synthetically produced aromatic hydrocarbon mixtures, thermally catalytically cracked hydrocarbon feedstocks, hydrocracked petroleum fractions or catalytically reformed hydrocarbons.

The fuel compositions according to the present invention may contain various other additives known in the art, such as:

(a) Anti-knock additives, such as lead compounds, or other compounds such as methyl cyclopentadienyl-manganese tricarbonyl or orthoazidophenyl.

(b) Co-antiknock additives, such as benzoylacetone.

(c) Dehazers, such as those commercially available as "NALCO" (trade mark) EC5462A (ex. Nalco), "TOLAD" (trade mark) 2683 (ex. Baker Petrolite), EXP177, EXP159M, EXP175, EP409 or EP435 (ex. RE Speciality Chemicals), and T9360-K, T9305, T9308, T9311 or T327 (ex. Baker Petrolite).

(d) Anti-foaming agents, such as those commercially available as "TEGOPREN" (trade mark) 5851, Q 25907, MR1027, MR2068 or MR2057 (ex. Dow Corning), "RHODORSIL" (trade mark) (ex. Rhone Poulenc), and "WITCO" (trade mark) SAG TP325 or SAG327 (ex. Witco).

(e) Ignition improvers (e.g. 2-ethylhexyl nitrate, cyclohexyl nitrate, di-tertiary-butyl peroxide and those disclosed in U.S. Pat. No. 4,208,190 at Column 2, line 27 to Column 3, line 21)

(f) Anti-rust agents (e.g. that commercially sold by Rhein Chemie, Mannheim, Germany as "RC 4801", or polyhydric alcohol esters of a succinic acid derivative, the succinic acid derivative having on at least one of its alpha carbon atoms an unsubstituted or substituted aliphatic hydrocarbon group containing from 20 to 500 carbon atoms (e.g. the pentaerythritol diester of polyisobutylene-substituted succinic acid)

(g) Reodorants.

(h) Anti-wear additives.

(i) Anti-oxidants (e.g. phenolics such as 2,6-di-tert-butylphenol, or phenylenediamines such as N,N'-di-sec-butyl-p-phenylenediamine).

(j) Metal deactivators.

(k) Lubricity agents, such as those commercially available as EC831, "PARADYNE" (trade mark) 631 or 655 (ex. Paramins) or "VEKTRON" (trade mark) 6010 (ex. Shell Additives International Limited).

(l) Carrier fluids such as a polyether e.g. a $C_{12}$–$C_{15}$ alkyl-substituted propylene glycol ("SAP 949"), "HVI" or "XHVI" (trade mark) base oil, which are commercially available from member companies of the Royal Dutch/Shell Group of Companies, a polyolefin derived from $C_2$–$C_6$ monomers, e.g. polyisobutylene having from 20 to 175, particularly 35 to 150, carbon atoms, or a polyalphaolefin having a viscosity at 100° C. in the range $2 \times 10^{-6}$ to $2 \times 10^{-5}$ m$^{-2}$/s (2 to 20 centistokes), being a hydrogenated oligomer containing 18 to 80 carbon atoms derived from at least one alphaolefinic monomer containing from 8 to 18 carbon atoms.

The lubricating oil and fuel compositions of the present invention may be prepared by adding the reaction product of the present invention to a lubricating base oil or base fuel. Conveniently, an additive concentrate is blended with the lubricating base oil or base fuel. Such a concentrate generally comprises an inert carrier fluid and one or more additives in a concentrated form. Hence the present invention also provides an additive concentrate comprising an inert carrier fluid and from 10 to 80% w (active matter) of a reaction product according to the present invention, the percentages by weight being based on the total weight of the concentrate.

Examples of inert carrier fluids include hydrocarbons and mixtures of hydrocarbons with alcohols or ethers, such as methanol, ethanol, propanol, 2-butoxyethanol or methyl tert-butyl ether. For example, the carrier fluid may be an aromatic hydrocarbon solvent such as toluene, xylene, mixtures thereof or mixtures of toluene or xylene with an alcohol. Alternatively, the carrier fluid may be a mineral base oil or mixture of mineral base oils, such as those sold by member companies of the Royal Dutch/Shell Group of Companies under the designations "HVI", e.g. "HVI 60" base oil, or the synthetic hydrocarbon base oils sold by member companies of the Royal Dutch/Shell Group of Companies under the designation "XHVI" (trade mark).

Non-limiting examples of suitable additive concentrations in final blended lubricating oil compositions are:

| Oil component % mass | A | B | C | D | E | F |
|---|---|---|---|---|---|---|
| Alkaline earth sulphonate detergent | 3.8 | 3.4 | — | — | — | — |
| Alkaline earth phenate detergent | 1.2 | 1.1 | — | — | — | — |
| Alkaline earth salicylate detergent | — | — | 4.6 | 2.5 | 3.6 | 10.5 |
| High molecular weight dispersant | — | 5.5 | 8.0 | 5.0 | 11.5 | — |
| Low molecular weight dispersant | 6.0 | 2.0 | — | — | — | 9.0 |
| Primary ZDTP | 0.5 | — | — | 0.3 | — | 0.7 |
| Secondary ZDTP | 0.4 | 1.0 | 0.9 | 0.7 | 1.2 | 0.6 |
| Aminic antioxidant | — | — | 0.6 | 0.8 | 0.3 | — |
| Phenolic antioxidant | 0.7 | 1.2 | — | — | — | — |
| Base oil | balance | balance | balance | balance | balance | balance |

Non-limiting examples of suitable additive concentrates for blending lubricating oil compositions are:

| Oil component % mass | A | B | C | D | E | F |
|---|---|---|---|---|---|---|
| Alkaline earth sulphonate detergent | 29.9 | 23.8 | — | — | — | — |
| Alkaline earth phenate detergent | 9.4 | 7.7 | — | — | — | — |
| Alkaline earth salicylate detergent | — | — | 32.4 | 26.6 | 21.6 | 50.2 |
| High molecular weight dispersant | — | 38.5 | 56.3 | 53.2 | 68.9 | — |
| Low molecular weight dispersant | 47.2 | 14.0 | — | — | — | 43.1 |
| Primary ZDTP | 3.9 | — | — | 3.2 | — | 3.3 |
| Secondary ZDTP | 3.1 | 7.0 | 6.3 | 7.4 | 7.2 | 2.9 |
| Aminic antioxidant | — | — | 4.2 | 8.5 | 1.8 | — |
| Phenolic antioxidant | 5.5 | 8.4 | — | — | — | — |
| Base oil | balance | balance | balance | balance | balance | balance |

The present invention still further provides the use of a reaction product according to the present invention as a dispersant additive.

The present invention will now be further described by reference to the following Examples. In these Examples, the number average molecular weight ($M_n$) specified for the polyisobutenyl moiety in the polyisobutenyl succinic anhydride (PIBSA) was determined by gel chromatography using polystyrene standards, e.g. as described in W. W. Yau, J. J. Kirkland and D. D. Bly, "Modern Size Exclusion Liquid Chromatography", John Wiley and Sons, New York, 21979.

Active matter content was determined by separating inactive material from the desired active matter on an aluminium oxide column using diethyl ether as eluant; and acid value was determined according to ASTM D 664.

EXAMPLE 1

PIBSA (PIB $M_n$ about 950, acid value 1.194 mmol H$^+$/g, active matter 56.8%) was added to TAHM (mol ratio PIBSA:TAHM 3:1) in toluene (2000 ml/mol TAHM), the mixture was azeotroped to remove water, toluene was distilled out and the mixture was finally heated to 200° C. for four hours. The product was diluted to 42% active matter with "HVI 60" oil.

EXAMPLES 2 to 9

These were prepared in a similar manner to Example 1; some were filtered to reduce haze where necessary.

Details of the reactants and reaction conditions for Examples 1 to 9 are shown in Table 1:

TABLE 1

| Example | $M_n$ of PIB in PIBSA | Molar ratio PIBSA:TAHM | Solvent | Reaction temp ° C. |
|---|---|---|---|---|
| 1 | ~950 | 3:1 | toluene | 200 |
| 2 | ~950 | 1:1 | toluene | 200 |
| 3 | ~950 | 2:1 | toluene | 200 |
| 4 | ~2100 | 1:1 | toluene | 200 |
| 5 | ~950 | 1.5:1 | toluene | 160 |
| 6 | ~950 | 1.5:1 | toluene | 200 |
| 7 | ~950 | 1.5:1 | toluene | 140 |
| 8 | ~950 | 1:1 | "SHELLSOL" A | 200 |
| 9 | ~950 | 1:1 | t-butanol | 200 |

EXAMPLE 10
Rheology Test

The products were tested for carbon black dispersancy using the Haake rheology test. This test used the Haake RV20 Rotary Viscometer and comprised adding a known concentration (2% w active matter) of the dispersant under test to a mixture of other compounds, to produce a fully formulated oil. Carbon black (a soot "mimic") was then added to result in a content of 4.76% w in the oil and mixed at an elevated temperature (90° C.) for a set period of time (at least 6 hours). The viscometric characteristics of the oils containing Examples 1 to 7 were then measured and compared under the same conditions, together with the commercial product "SAP 286" (mono/bis PIB succinimide, ex Shell Additives International Limited).

The base oil blends used in the Haake rheology test consisted of the following components:

| Component | Concentration % w |
|---|---|
| Detergents (overbased calcium and magnesium alkyl salicylates) | 3.5 |
| Anti-wear additive (zinc dithiophosphate (ZDTP)) | 1.13 |
| Viscosity index improver (hydrogenated polyisoprene) | 5.88 |
| Pour point depressant (polymethacrylate) | 0.34 |
| Mixture of base oils | 89.15 |

The Haake rheology test apparatus comprises a Haake RV 20 rheometer with RC 20 rheocontroller and CV 100 measuring system with a ZA 30 cup and rotor.

The samples were prepared by weighing (100/active matter)g of the dispersant sample, made up to 5.75 g with HVI-60-AL base oil, and then 50 g total mass with the base oil blend.

The carbon black (grade XC72) was activated at 140° C. for at least 12 hours prior to use in the rheology test. An amount, 0.25 to 0.30 g, of the carbon black was measured, and fully formulated oil was added in an amount as calculated by the formula:

$$M_{FFO} = M_C \times 20$$

where $M_C$ is the mass of the fully formulated oil (g), and $M_C$ is the mass of carbon black (g). The mixture was completely homogenised with the oil. The viscosity characteristics were measured after at least 6 hours at 90° C. over a range of shear rates for 30 minutes.

The results of the rheology tests using 2% w active matter of each of Examples 1 to 7 and "SAP 286" are shown in FIG. 1, from which it can be seen that all of the Examples exhibit higher dispersancy than that of "SAP 286".

EXAMPLE 11

Rheology Test

Figure 2:
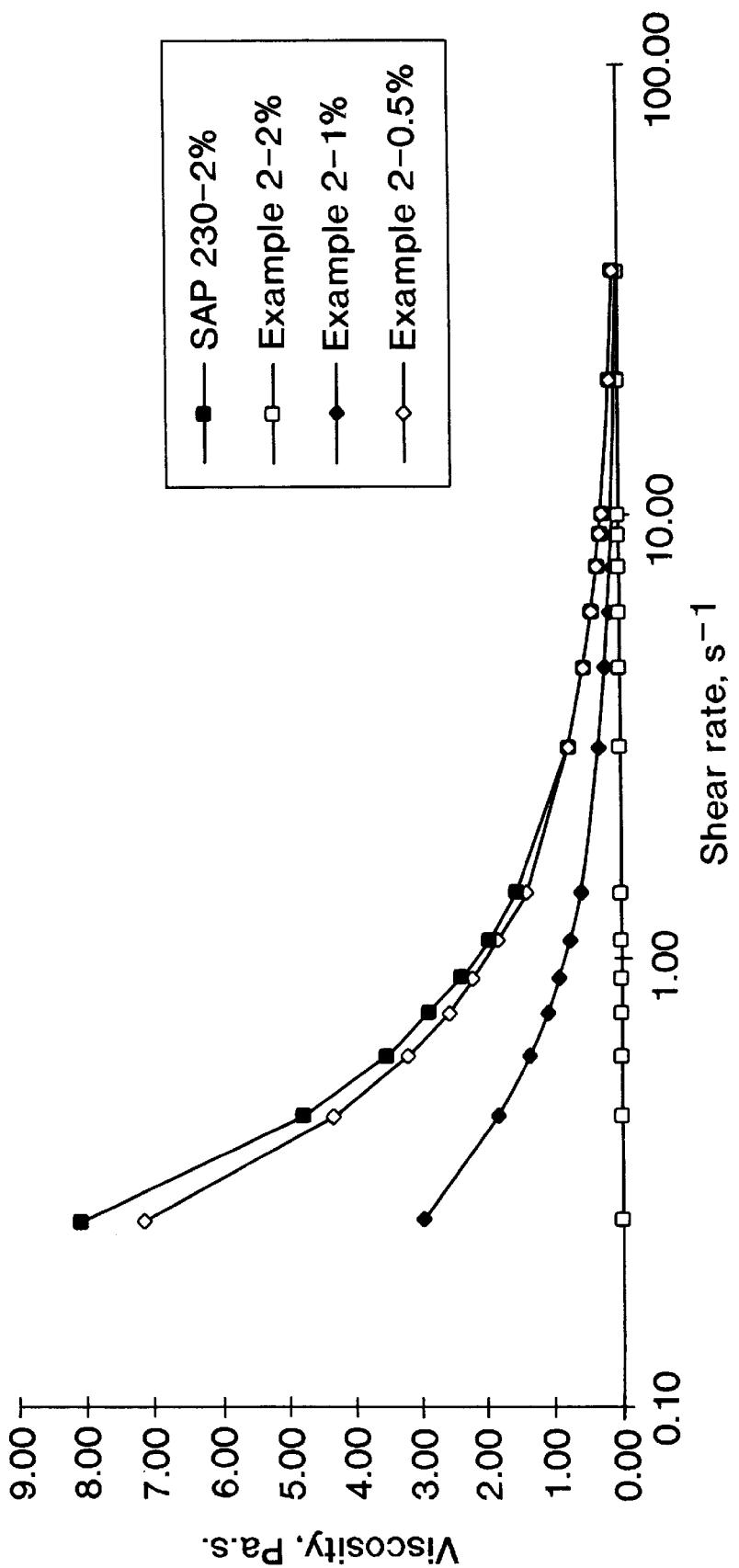

Further Haake rheology testing, as described above, was carried out on Example 2 at the concentrations 0.5% w, 1% w and 2% w active matter and the commercial product "SAP 230" (mono/bis- PIB succinimide, ex Shall Additives International Limited) at the concentration 2% w active matter. The results of the tests are shown in FIG. 2, from which it can be seen that at all concentrations Example 2 exhibits higher dispersancy than "SAP 230".

EXAMPLE 12

Fluoroelastomer Seals Test

Reaction products of the present invention are not unduly aggressive to fluoroelastomer seals, as demonstrated in the Mercedes-Benz fluoroelastomer seals test. When seal fluoroelastomer was subjected to a formulation containing 6.75% w of Example 2 its tensile strength was reduced by only 38.1% and the extent to which it could be stretched before breaking was reduced by only 39.5%.

EXAMPLE 13

Corrosion Test

Reaction products of the present invention display low corrosion, as demonstrated in the L-10 corrosion test without severity adjustment (ref. API CG-4 test). When Example 2 was incorporated in the test lubricant formulation at 6.75% w, the measured metal content of the lubricant after the test was: copper 5 ppm, lead 38 ppm and tin <1 ppm.

EXAMPLE 14

Figure 3:
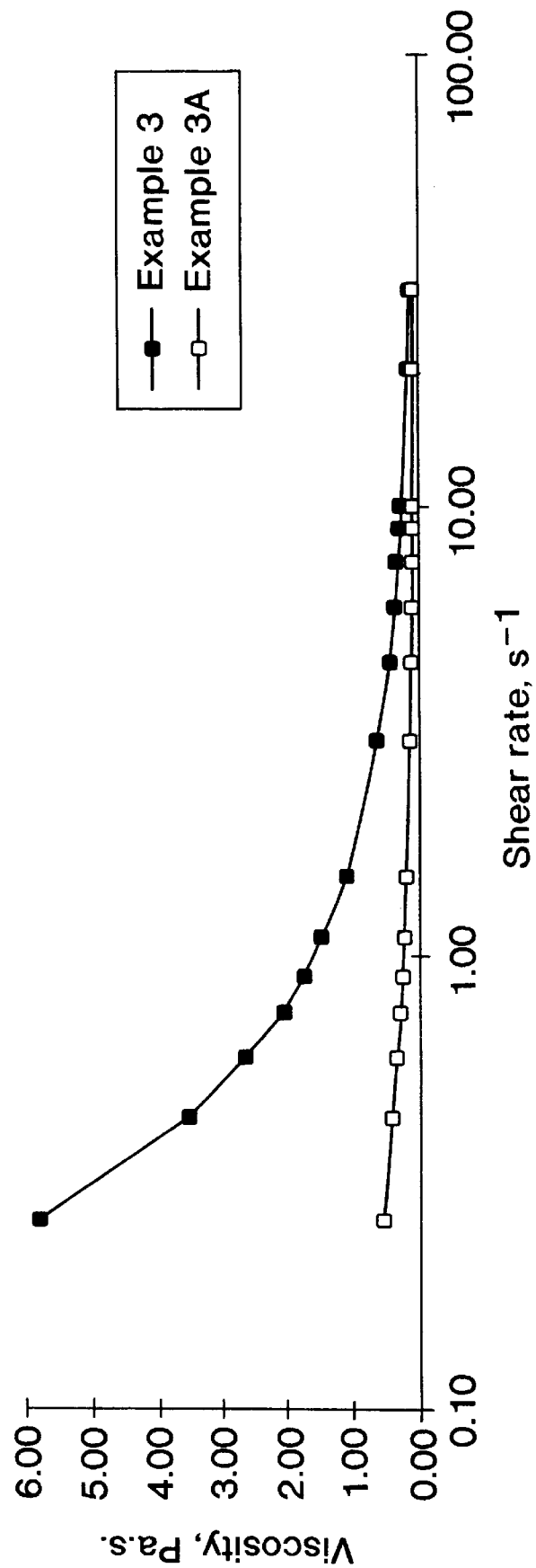

Example 3, which had been prepared using a PIBSA in which the PIB contained about 5% of terminal vinylidene unsaturation, was repeated (Example 3A) but using PIB having a high level of terminal vinylidene unsaturation (about 90%) ("GLISSOPAL 1000" ex BASF). The PIB $M_n$ was about 1000, the acid value was 1.444 mmol H$^+$/g and the active matter was 56.7%. The above described rheology testing was carried out at 2% w active matter dispersant concentration to compare the dispersancy of Examples 3 and 3A. The results are shown in FIG. 3, from which it can be seen that Example 3A, the product of a polyfunctional reactant with a PIBSA of relatively high acid value, derived from a PIB having a high level of terminal vinylidene unsaturation, exhibits higher dispersancy than Example 3.

What is claimed is:

1. The reaction product of:
   (i) a polyalkenyl derivative of an ethylenically unsaturated carboxylic reagent and
   (ii) a compound of the formula

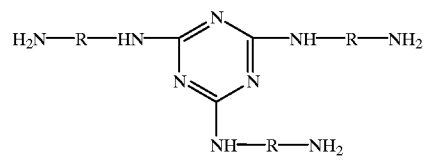

wherein R is a linear alkylene group having at least 2 carbon atoms, a branched alkylene group having at least 3 carbon atoms, a cycloalkylene group having at least 5 carbon atoms, in which one or more of said carbon atoms may be substituted by one or more hetero atoms, or is an aromatic group or a group of the formula

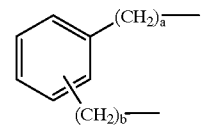

in which a is 1 to 6 and b is 0 to 6, wherein the groups R may be the same or different, and wherein the values of a and b may be the same or different.

2. A reaction product according to claim 1, wherein the ethylenically unsaturated carboxylic reagent is selected from monoethylenically unsaturated $C_{4-10}$ dicarboxylic acids and anhydrides.

3. A reaction product according to claim 1, wherein the polyalkenyl derivative is derived from a polyalkene which is a polymer of at least one $C_{2-10}$ monoolefin.

4. A reaction product according to claim 1, wherein R is a $C_{2-10}$ linear alkylene group.

5. A reaction product according to claim 4 wherein R is a $C_6$ linear alkylene group.

6. A process for the preparation of a reaction product according to claim 1, which comprises reacting
   (i) a polyalkenyl derivative of an ethylenically unsaturated carboxylic reagent and
   (ii) a compound of the formula

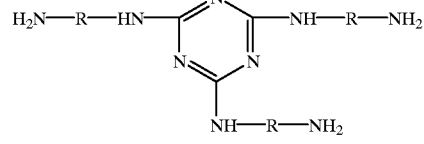

wherein R is a linear alkylene group having at least 2 carbon atoms, a branched alkylene group having at least 3 carbon atoms, a cycloalkylene group having at least 5 carbon atoms, in which one or more of said carbon atoms may be substituted by one or more hetero atoms, or is an aromatic group or a group of the formula

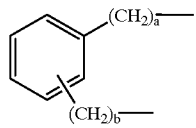

in which a is 1 to 6 and b is 0 to 6, wherein the groups R may be the same or different, and wherein the values of a and b may be the same or different.

7. A process according to claim 6 wherein the reaction temperature is 120 to 240° C.

8. A process according to claim 6 which is carried out in the presence of an inert solvent.

9. A lubricating oil composition comprising a major amount of a lubricating base oil and a minor amount of a reaction product according to claim 1.

10. An additive concentrate comprising an inert carrier fluid and from 10 to 80% w, based on the total concentrate, of a reaction product according to claim 1.

* * * * *